United States Patent [19]

Ison

[11] Patent Number: Plant 7,266

[45] Date of Patent: Jul. 10, 1990

[54] PINEAPPLE

[76] Inventor: William G. Ison, Rte. 1, Box 19, Hwy. 19, Brooks, Ga. 30205

[21] Appl. No.: 166,243

[22] Filed: Mar. 10, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety Fry and the pollen parent variety Senoia to produce an improved variety of self-fertile muscadine grape.

1 Drawing Sheet

DESCRIPTION OF THE VARIETY

A cross between the female variety Fry and the pollen parent variety Senoia.

The primary objective of the breeding was to produce an improved variety of muscadine grape; the fruit of which would have superior characteristics for fresh fruit, high quality, 100% dry scar for longer shelf life; for high sugar content; for wine purposes; and the plant to be vigorous and productive.

In comparison with both the seed and pollen parent, the new variety is similar in flavor and color to the pollen parent; similar in size and sugar content to the seed parent. The new variety is higher in sugar content than the pollen parent, containing average 21% soluble solids. An outstanding characteristic of this variety is the Pineapple taste. The new variety has very long stems and very long clusters. The present variety yields on the average of 8 to 12 tons per acre in tests conducted at Ison's Nursery & Vineyards, Brooks, Ga.

Asexual reproduction of the new variety either by soft-wood cuttings or by layering as performed at Brooks, Ga. shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of the characters.

The following is a detailed description of the new variety:

Species: *Vitis rotundifolia.*
Type: Vine.
Seed parent: Variety Fry.

Pollen parent: Variety Senoia.
Propagation: Holds its characteristics through succeeding propagation by either layering or by soft-wood cuttings.
Locality where grown: Brooks, Ga.
Fruit borne: In clusters of approximately 8 to 25 berries per cluster.
Fruit size: Large, similar in size to the seed parent; diameter 1⅛" approximately.
Fruit color: Greyed Yellow Group #161 A Fan 4 of the Royal Horticultural Society, London, England.
Sugar content: 20.50 to 21.50 percent soluble solids.
Shape: Oblong.
Seed: Average diameter ⅛"; average seed per berry 2.65.
Skin: Thick.
Growth habits: Vine vigorous, very productive, requires support.
Pulp: A. Color Group Greyed Green #193A Fan 4 Royal Horticultural Society, London, England. B. Consistency, medium firm, tender and juicy # as compared to most muscadine varieties.
Foliage: Leaf Color, Green Group 136B Fan 3 Royal Horticultural Society London, England. Leaf size and shape similar to most muscadine varieties.
Reproductive organs: Self-pollinating.
Canes: Small to medium.
Maturity date: Usually ripens about October 1 at Brooks, Ga.
Diseases: Tolerant to diseases; slightly susceptible to Black Rot.

This description was made from a muscadine vine grown at Ison's Nursery & Vineyards, Brooks, Ga.

I claim:

1. The new and distinct variety of the grape plant as described and illustrated.

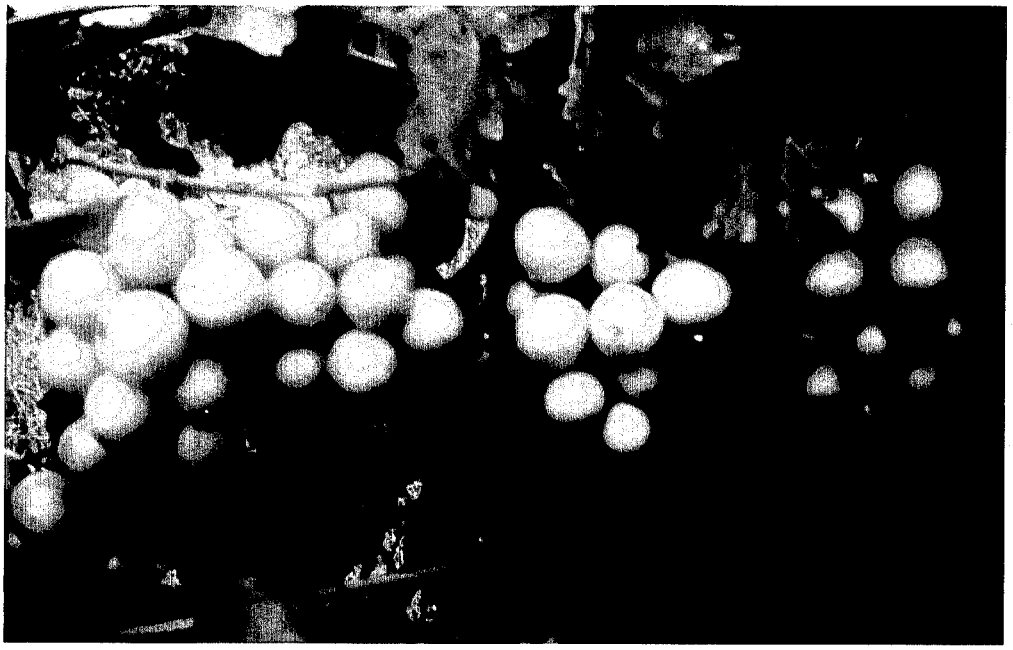

* * * * *